United States Patent [19]
Bell

[11] Patent Number: 5,853,391
[45] Date of Patent: Dec. 29, 1998

[54] SLOTTED REGIONAL ANESTHESIA NEEDLE

[75] Inventor: Craig J. Bell, E. Swanzey, N.H.

[73] Assignee: Medcare Medical Group, Inc., E. Swanzey, N.H.

[21] Appl. No.: 673,510

[22] Filed: Jul. 1, 1996

[51] Int. Cl.$^6$ ................................................. A61M 5/178

[52] U.S. Cl. .................... 604/160; 604/158; 604/164; 604/166

[58] Field of Search .................... 604/158, 160, 604/161, 164, 165, 166, 169, 177

[56] References Cited

U.S. PATENT DOCUMENTS

| | | | |
|---|---|---|---|
| 3,682,173 | 8/1972 | Center | 604/160 X |
| 3,827,434 | 8/1974 | Thompson et al. | 604/160 |
| 4,354,491 | 10/1982 | Marbry | 604/160 |
| 5,380,290 | 1/1995 | Makower et al. | 604/164 |
| 5,425,717 | 6/1995 | Mohiuddin | 604/160 |

*Primary Examiner*—Sam Rimell
*Assistant Examiner*—Robert V. Racunas
*Attorney, Agent, or Firm*—George W. Dishong

[57] ABSTRACT

A hypodermic needle device for administration of anesthesia to a patient's epidural space comprising a hypodermic needle having a barrel portion with opposed distal and proximal ends, a hub assembly located at the proximal end of the barrel portion of the needle, through which instruments such as a rigid stylet, or a flexible catheter having a pre-affixed connector, may be introduced into the needle, and a slot formed axially along the length of the needle from the distal end through the hub at the proximal end of the needle. The slot has a minimum width dimension not greater than the outer diameter of a stylet or epidural catheter such that during location of the epidural space, and placement of a catheter in the epidural space, the stylet and catheter will not come out of the needle, yet the needle may be easily removed from the catheter once the catheter is in place, by pulling the catheter through the slot in the needle.

7 Claims, 6 Drawing Sheets

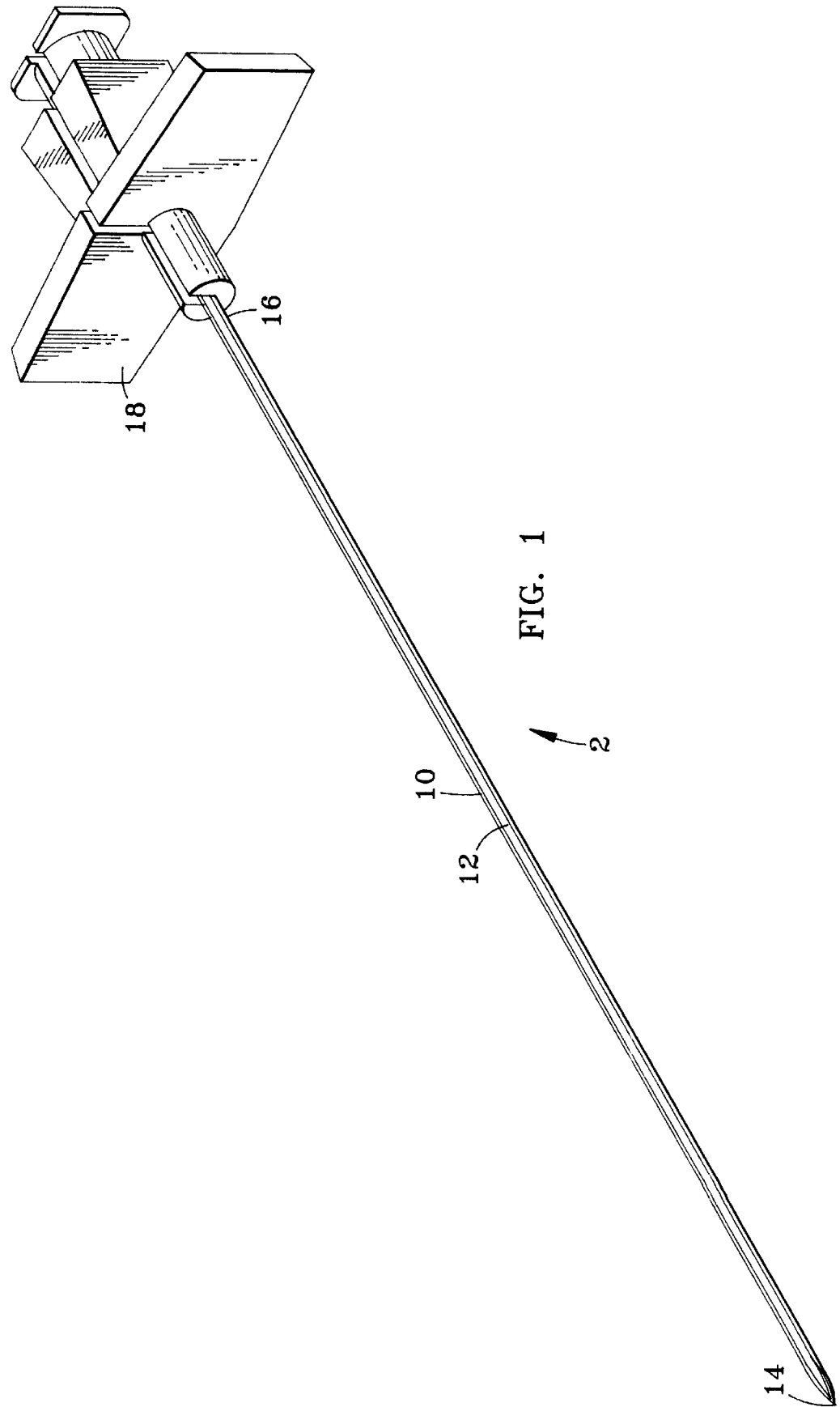

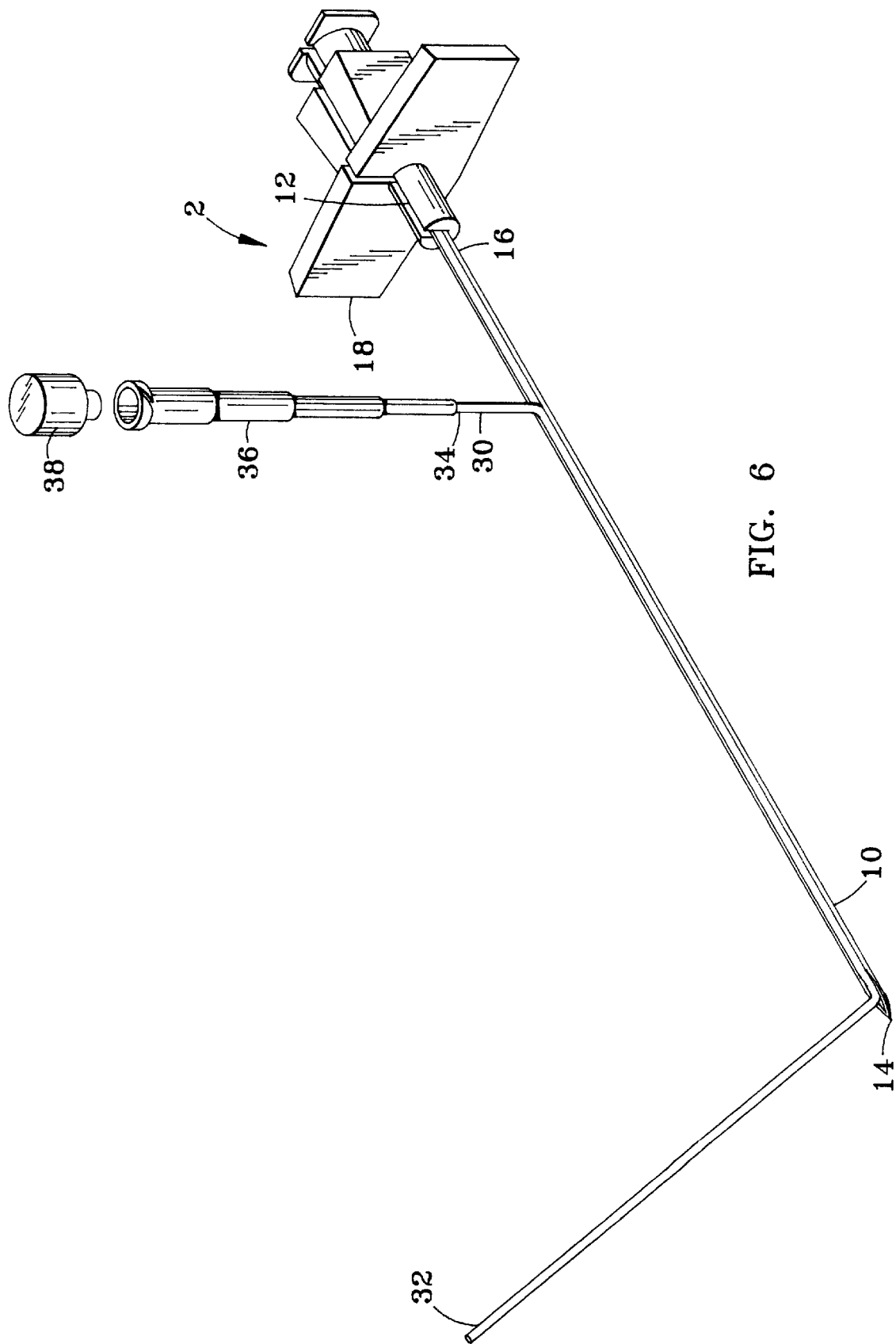

SLOTTED REGIONAL ANESTHESIA NEEDLE

BACKGROUND OF THE INVENTION

1. Field of the Invention

This invention most generally relates to anesthesia needles used to administer regional anesthesia to a patient. More particularly the invention relates to a regional anesthesia needle used to apply anesthesia to the epidural space of a patient. Most particularly the invention relates to an epidural anesthesia needle having a slot running the length of the needle from the distal end through a hub at the proximal end. The slot allows the use of a catheter with a permanently pre-affixed connector at its proximal end for administration of anesthesia to a patient. The slot is formed with a dimension that is smaller than the outer diameter of a stylet and catheter. The smaller diameter prevents the stylet and catheter from inadvertently coming out of the needle during the procedure. Once the catheter is in place in the epidural space of a patient and secured, the needle is withdrawn and can be removed by pulling the flexible catheter out of the slot in the needle, thus allowing the use of a catheter with a permanently pre-affixed connector at its proximal end.

2. Description of the Prior Art

Regional anesthesia is performed to bring about anesthesia in a specific region of the body. The patient remains conscious of his surroundings and may retain complete mobility of the area anesthetized. When successfully performed, regional anesthesia provides complete analgesia in the specific area to which it was directed and requires only a small amount of local anesthetic. The regional anesthesia relevant to the present invention relates specifically to spinal anesthesia delivered to the epidural space, as related to the cervical, thoracic, lumbar, or caudal regions of the spine, but more specifically to the regional anesthesia performed in the lumbar or thoracic regions.

There are many preparative steps before administration of the anesthesia. The general technique of administering epidural anesthesia involves injecting a local anesthetic solution into the epidural space, from which it defuses to the immediate vertebral spaces around the injection site and around the outer layers of the spinal cord, surrounding spinal nerves, producing anesthesia. The technique is most commonly performed at the lumbar level of the spine and is applicable in the diagnosis and treatment of chronic pain, for example in cancer patients, as well as providing surgical and obstetric anesthesia.

The epidural space extends from the base of the skull to the tip of the caudal vertebrae, and lies between the dura which surrounds the spinal cord and the ligaments which join the vertebrae. The epidural space is not considered a true space, because unless separated, it is practically invisible.

Before administering the anesthesia to the epidural space, the space must first be located, and care taken not to penetrate to the spinal cord. There are two different techniques which can be used to determine when the tip of the needle has entered the epidural space; the "hanging drop", and "loss of resistance" techniques. An epidural needle is first inserted until a marked resistance is felt, indicating entry into the interspinous ligament, and up to but not through, the ligamentum flavum. At this point, in the "loss of resistance" technique, the epidural needle is advanced into the ligamentum flavum, and the stylet is removed. A syringe with an easily moving plunger is filled with air or normal saline and attached to the needle. When the needle tip is in the ligamentum flavum, air or saline can not be ejected from the syringe when pressure is applied to the plunger. Constant pressure is exerted on the plunger by one hand as the needle is slowly advanced. When the tip of the needle enters the epidural space, there is a sudden release of air or saline into the epidural space, thus the loss of resistance. Once the epidural space is located, the syringe is removed and a catheter is placed onto the needle hub, and then inserted through the epidural needle, between about 2 cm to about 4 cm past the end of the needle, into the epidural space. When the catheter is in place, the needle is then withdrawn over the catheter taking care not to move the catheter. Once the catheter is advanced past the tip of the needle the catheter cannot be withdrawn because it might be sheared by the sharp tip of the needle. If readjustment is needed, both needle and catheter must be removed together. An epidural catheter connector is then attached to the catheter to allow syringe attachment for administration of anesthesia through the catheter. The catheter is then taped in place on the patient's back.

With the above procedure in which the needle is removed by being slid over the catheter, the catheter can not have a connector "built in" or preaffixed to its proximal end because the needle would not fit over the connector. The typical connector is placed on the catheter after the needle is removed. The connector is comprised of three parts, two that are threaded together sandwiching the third part, an elastomeric tube. The catheter is slid into the connector going through the elastomeric tube. When the two threaded parts are tightened together the elastomeric tube is compressed, so its inside diameter (ID) squeezes the catheter outside diameter (OD). The problems with attaching a connector to the catheter at the time of treatment are that the connector can be over-tightened, crushing the catheter or it can be under-tightened creating a leak path or leading to the connector falling off the catheter potentially exposing the patient to extrinsic contamination. The procedure is cumbersome and the person performing the treatment may drop the connector during installation. A solution would be to have a catheter with a connector permanently or preaffixed to its proximal end by the manufacturer or at least prior to insertion of the catheter into the needle. However, the typical needle cannot be removed over a permanently or preaffixed connector.

One solution was advanced by Mohiuddin in U.S. Pat. Nos. 5,322,512 (the '512 patent) and 5,425,717 (the '717 patent). Mohiuddin's solution was to have a needle which was splittable and could break away from the catheter. The needle is removed from the catheter by breaking the needle in half along its length. Both the '512 and the '717 patents address this issue. The '512 patent deals with protecting the splittable needle, and the second includes with the splittable needle a catheter with a fixed connector. This needle can be used with a catheter having a permanently affixed connector, but presents its own problems. These problems include; the needle not splitting all the way, preventing its removal from the catheter as intended, and the needle splitting prematurely while still in the patient during placement, preventing catheter placement until the split needle is removed and another needle placed. The present invention solves the problems of the prior art by providing an epidural anesthesia needle which may be more efficiently and safely used with a catheter having a permanently affixed connector.

SUMMARY OF THE INVENTION

A slotted hypodermic regional epidural anesthesia needle having a barrel portion with opposing distal and proximal ends and a hub at the proximal end, having a slot formed axially in the barrel portion running from the distal end all the way through the hub at the proximal end of the needle. The slot has a minimum width dimension that is smaller than the outer diameter of a typical stylet and catheter used in such a procedure. The smaller diameter of the slot prevents the stylet and catheter from inadvertently coming out of the slot in the needle during placement of the catheter. In order to allow the use of the "loss of resistance" technique for location of the epidural space, and use of a syringe without removing the stylet from the needle, the stylet used with the present invention has a female luer fitment on its proximal end for connection to a syringe and is constructed of hypodermic cannula.

The slotted hypodermic regional epidural anesthesia needle is placed in the same manner as current anesthesia needles, with the exception of not having to remove the stylet to perform the "loss of resistance" technique because the stylet is hollow. Once the tip of the needle is in the epidural space, the stylet is removed and the epidural catheter, with a connector and cap affixed, is passed through the needle and positioned in the epidural space. The slotted hypodermic regional anesthesia needle is then pulled out of the patient and slid to the proximal end of the catheter. The catheter is secured to the patient to prevent it from moving. The needle is then removed by pulling the catheter out through the slot in the needle starting at one end of the needle and working toward the opposite end.

Objects and advantages of the invention are: 1.) Elimination of catheter crushing from over tightening connectors; 2.) Elimination of catheter leakage from under tightening of connector; 3.) Elimination of inadvertent disconnection of connector; 4.) Reduced potential for contamination and infection; 5.) Reduced number of procedural steps; 6.) Allowance of use of catheter a with pre-affixed connector; 7.) No splitting of the needle is required; 8.) The slot is not subject to malfunction resulting in not being able to remove the needle from the catheter; 9.) The slot is not subject to premature malfunction (splitting) during needle placement; and 10.) Use of a cannulated stylet allows the "loss of resistance" technique to be performed without removing the stylet, resulting in less procedural steps.

A primary object of the invention is to provide a slotted hypodermic regional anesthesia needle that can be used with a catheter having a pre-affixed connector, may be easily removed from the catheter, and does not have to be broken or split in order to be removed from the catheter.

Yet another primary object of the invention is to provide a slotted hypodermic regional anesthesia needle through which a stylet and catheter may be placed without concern that the stylet or catheter will inadvertently come out of the catheter prematurely during placement into the patient.

A particular object of the present invention is to provide a slotted hypodermic regional anesthesia needle for use with a catheter having a pre-affixed connector such that the problems associated with manually attaching a connector, such as over or under tightening of the connector, inadvertent disconnection of the connector, and greater potential for contamination and infection due to handling of more components, are eliminated.

A further particular element of the present invention is to provide a slotted hypodermic regional anesthesia needle which reduces the number of procedural steps required to place a catheter in the epidural space of a patient in order to administer anesthesia.

These and further objects of the present invention will become apparent to those skilled in the art to which this invention pertains and after a study of the present disclosure of the invention.

BRIEF DESCRIPTION OF THE DRAWINGS

FIG. 1 is an isometric view of the present invention;

FIG. 6 is an isometric view of the present invention showing the removal of the catheter from the needle once the catheter is in place in the epidural space of a patient.

DESCRIPTION OF THE PREFERRED EMBODIMENTS

Figure 2B:
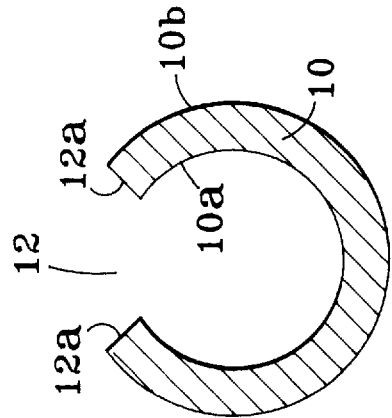
FIGS. 2a–2d are cross sections showing various shapes and dimensions of the slot of the present invention.

The following is a description of the preferred embodiment of the invention. It is clear that there may be variations in the size and the shape of the device and in the materials used in the construction and in the orientation of the various components which make up the anethesia needle device.

Reference is now made to FIG. 1 which shows the slotted hypodermic regional anesthesia needle 2 of the present invention. Needle 2 is similar in diameter, material and length to the type typically used for administration of epidural anesthesia. I.e., the typical needle is 17 gauge and 3½ inches long. Needle 2 contains a barrel portion 10, distal end 14 which is inserted into the patient, proximal end 16 which remains outside the patient. There is a hub 18 at the proximal end 16 of barrel portion 10, and a slot 12 running axially along the length of barrel portion 10, through hub 18 resulting in slotted hypodermic regional anesthesia needle 2.

Figure 2D:
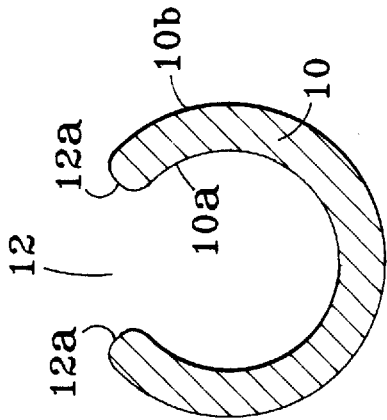
Figure 2A:
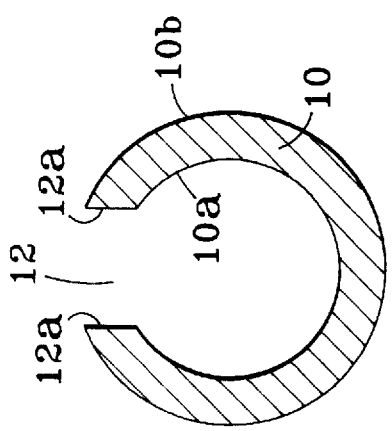
Figure 2C:
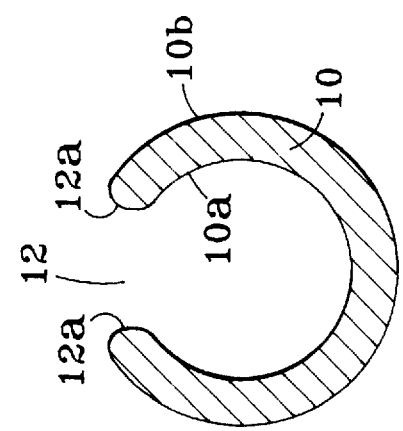
Figure 2:
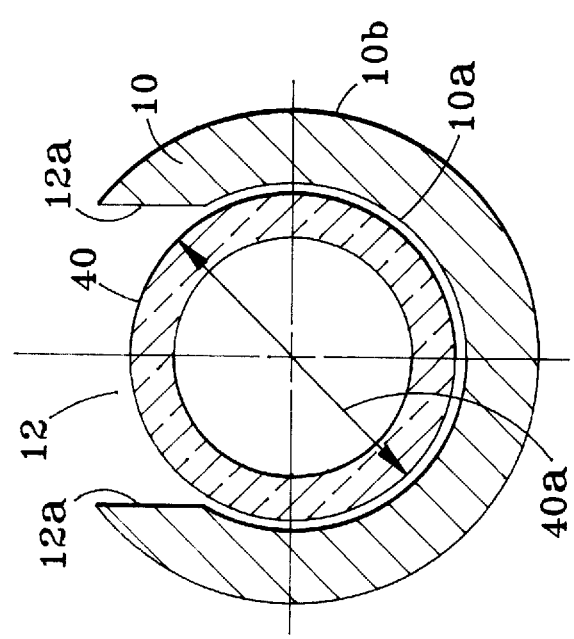
FIG. 2. is a cross section of the present invention showing a catheter or stylet in place within the slotted needle.
Figure 3:
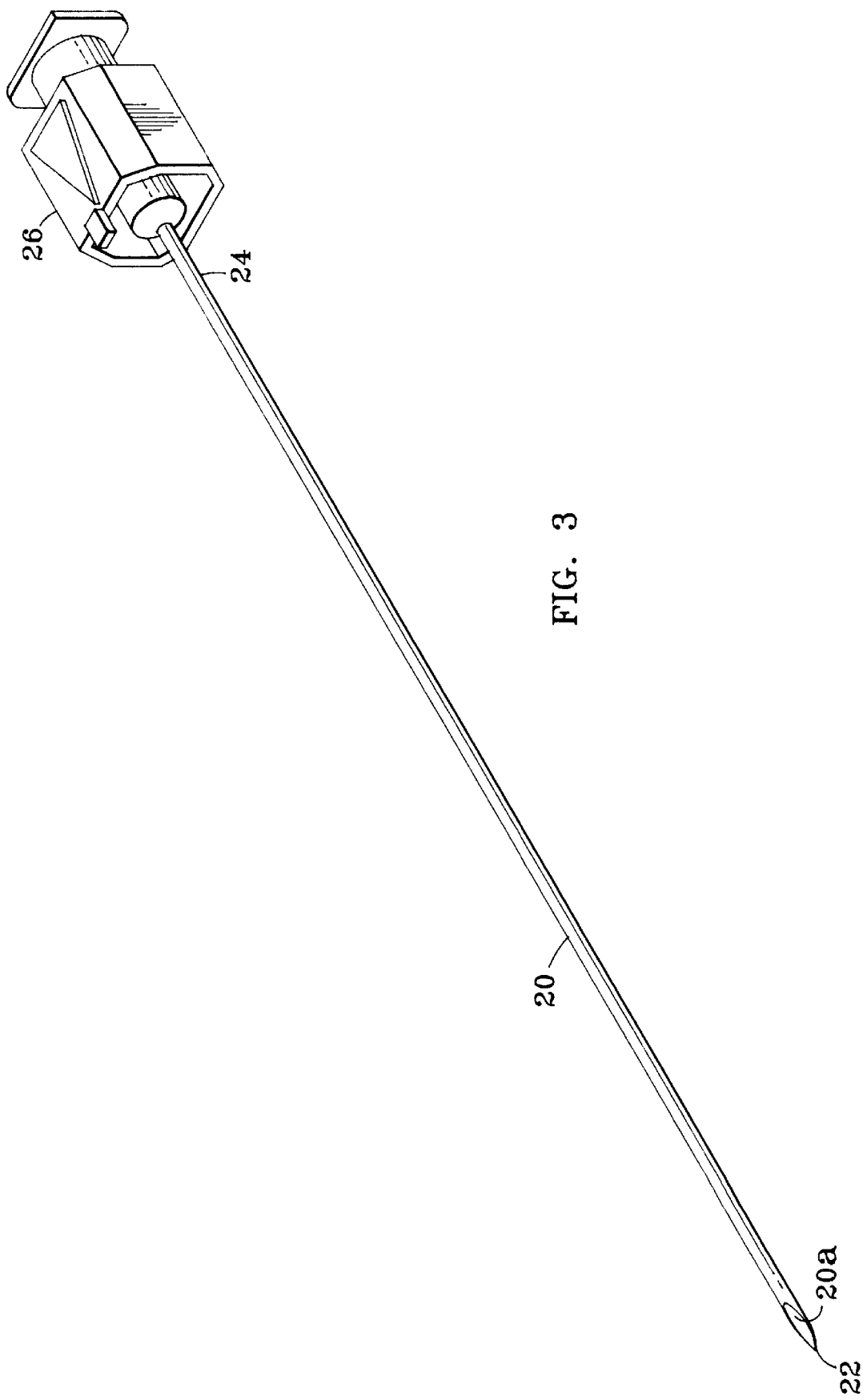
FIG. 3. is an isometric view of a cannulated stylet as used in the present invention.
Figure 4:
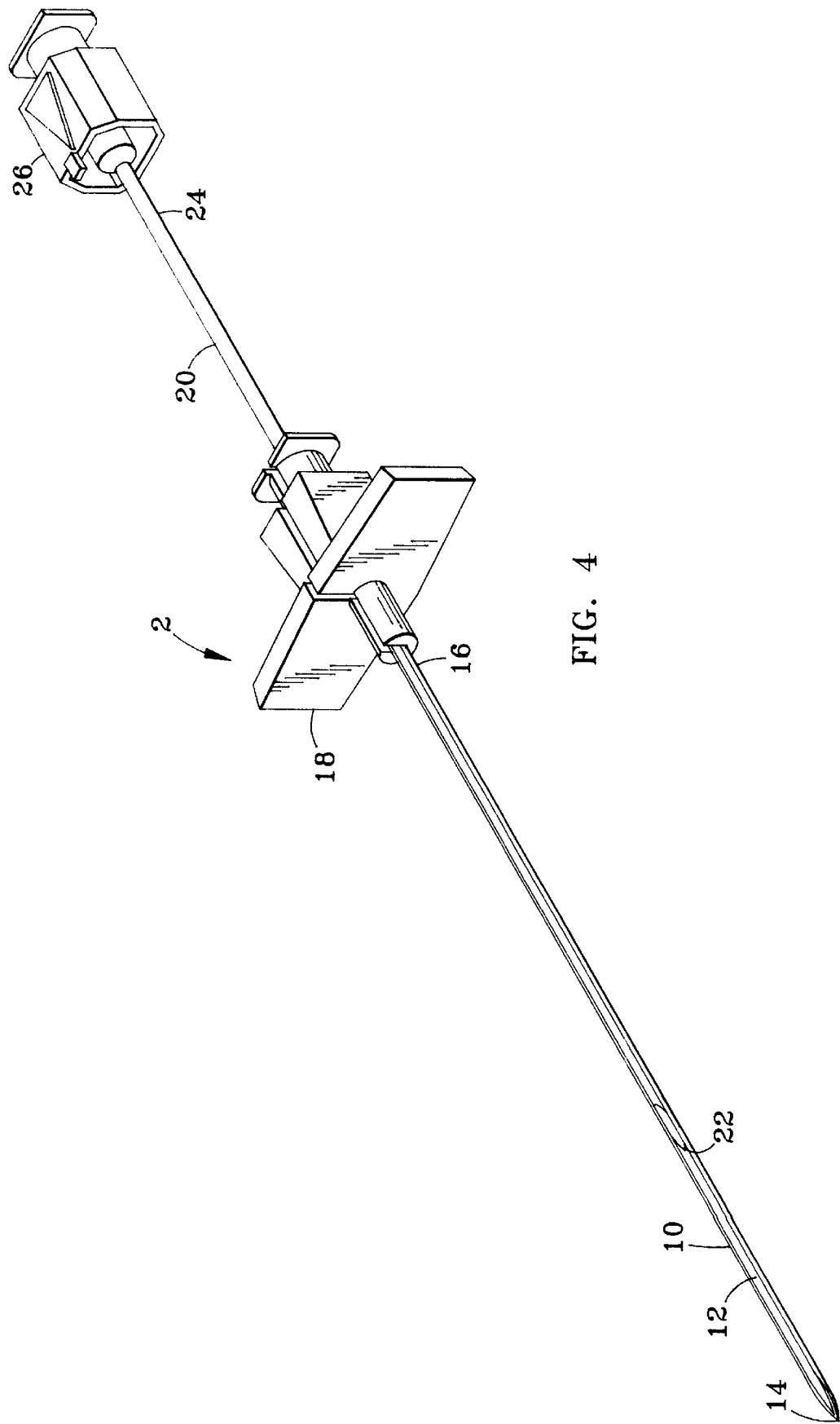
FIG. 4 shows a stylet positioned partially in the slotted needle of the present invention.
Figure 5:
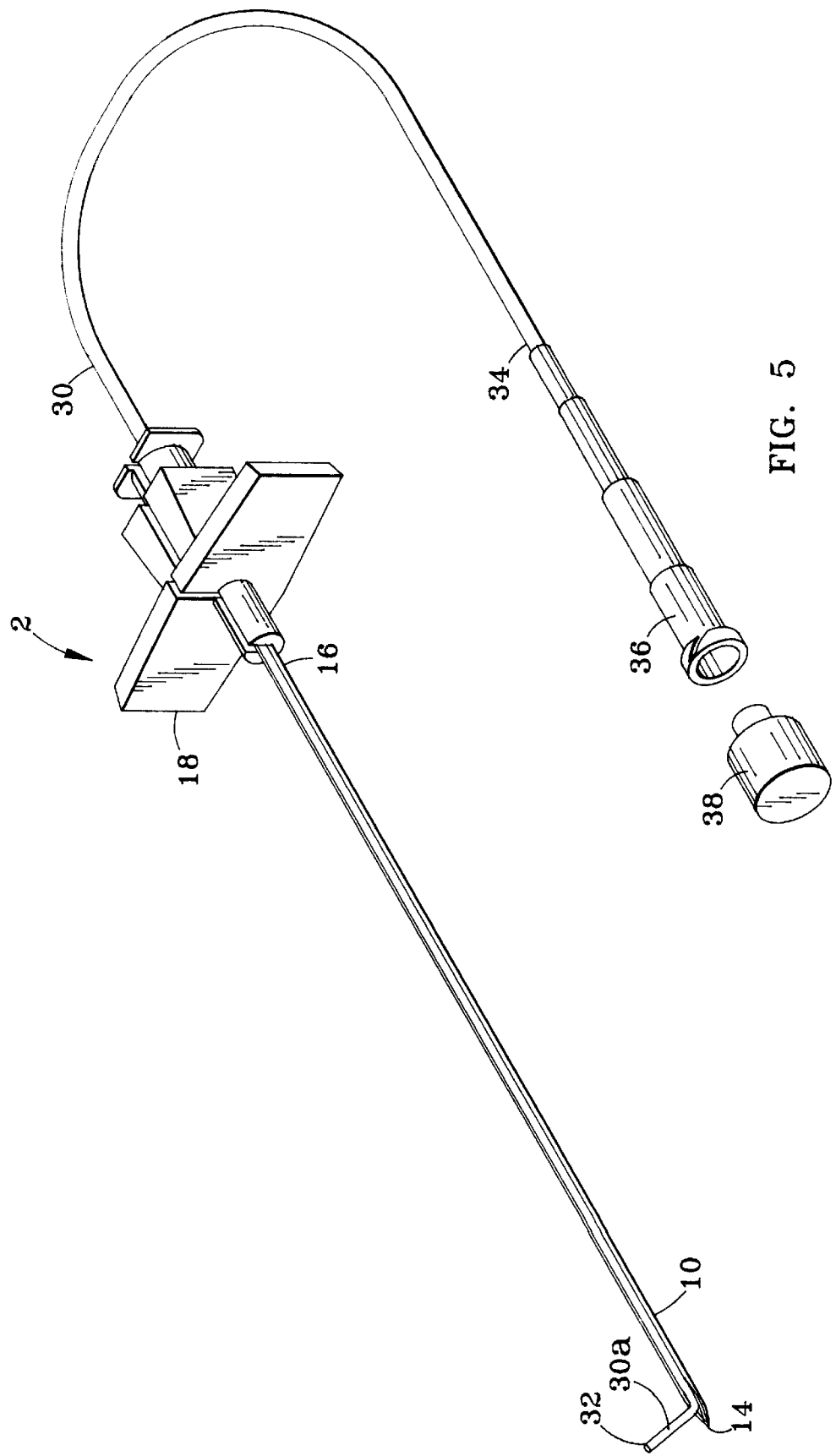
FIG. 5 is an isometric view of the present invention showing a catheter, having a pre-affixed connector, positioned inside the slotted hypodermic regional anesthesia needle.

FIGS. 2–6 illustrate, by sketch, particular embodiments and features of the present invention. FIG. 2 is a cross section of barrel portion 10 of needle 2 showing inner and outer walls 10a and 10b of barrel portion 10, and slot 12 with an instrument 40 having an outer diameter 40a, such as a stylet 20 having an outer diameter 20a as shown in FIG. 3 or a catheter 30 having an outer diameter 30a as shown in FIG. 5, inserted in barrel portion 10 of needle 2. Epidural catheter 30 is typically a 19 gauge tube made of nylon, polyurethane, or fluorinated ethylene propylene (FEP). Slot 12 has opposing walls 12a and the distance between walls 12a must be smaller in width than the outer diameter of either a typical solid or cannulated stylet or typical flexible epidural catheter at at least one area along slot 12, such that stylet 20 or catheter 30 can not simply "pop" out of needle 2 through slot 12.

FIGS. 2a–2d show cross sections of various configurations and dimensions of slot 12. Although some portion of slot 12 must be smaller in width than the outer diameter of either a stylet or catheter to prevent the stylet or catheter from dislodging, slot 12 may vary in width along the length of barrel portion 10 as long as catheter 30 will not dislodge yet is removable through slot 12. Slot 12 could be cut such that walls 12a are parallel, or non-parallel as shown in FIGS. 2a and 2b. Walls 12a may be radiused or rounded where they meet inner and outer walls 10a and 10b of barrel portion 10 of needle 2 and hub 18 as shown in FIGS. 2c and 2d.

FIG. 3 illustrates the particular type of stylet 20 to be used with the present invention. Stylet 20 is cannulated, hollow, and helps keep needle 2 rigid and clear of debris. Stylet 20 has a distal end 22 and a proximal end 24 to which is attached a female luer fitment 26, such that a syringe (not shown) may be attached to the luer for performance of the "loss of resistance" technique to locate the epidural space of a patient.

FIG. 4 shows stylet 20 partially in place in slotted regional anesthesia needle 2. FIG. 5 illustrates needle 2 with an epidural catheter 30 in place in needle 2. Catheter 30 passes through hub 18 into slot 12 in needle 2. Catheter 30 has a distal end 32 which extends from about 2 cm to about 4 cm past the distal end of the tip of needle 2 when fully inserted, and a proximal end 34 at which is attached a pre-affixed connector 36 to place catheter 30 in fluid communication with a source of liquid anesthesia for administering to the patient. There is a cap 38 which fits connector 36 to close connector 36 and protect against contamination when anesthesia is not being administered.

FIG. 6 shows the process of removing needle 2 from catheter 30 once catheter 30 is in place in the epidural space in the patient and needle 2 has been withdrawn. Catheter 30 may be pulled from needle 2 by pulling flexible catheter 30 through slot 12 which runs the entire length of needle 2, including running through hub 18. In this way, once catheter 30 is in place in the epidural space, needle 2 may be withdrawn from the patient, secured to the patient, and needle 2 removed in one piece, leaving the catheter 30 with its pre-affixed connector 36 ready to receive anesthesia.

With the present invention, the step of removing stylet 20 in order to perform the "loss of resistance" technique to locate the epidural space is eliminated. More importantly, the step of manually attaching a connector to proximal end 34 of catheter 30 after insertion of catheter 30 and removal of needle 2 is eliminated. Needle 2 is easily removed leaving catheter 30 with pre-affixed connector 36 in place.

It is thought that the present slotted regional anesthesia needle, for use in the administration of anesthesia to the epidural space of a patient and many of its attendant advantages is understood from the foregoing description and it will be apparent that various changes may be made in the form, construction and arrangement of the parts thereof without departing from the spirit and scope of the invention or sacrificing all of its material advantages, the form herein before described being merely a preferred or exemplary embodiment thereof.

I claim:

1. A hypodermic needle device comprising:

a hypodermic needle having a barrel portion with inner and outer walls and a distal end and an opposed proximal end;

a slot axially directed along the length of said hypodermic needle from said distal end to said opposed proximal end, said slot having a minimum width dimension; and an instrument having an instrument outer diameter, an instrument distal end and an instrument proximal end, inserted into said hypodermic needle device, said instrument comprising a hollow, cannulated stylet, and said slot minimum width dimension being less than said instrument outer diameter and not less than a dimension through which said hollow cannulated stylet can pass therethrough.

2. A hypodermic needle device comprising:

a hypodermic needle having a barrel portion with inner and outer walls and a distal end and an opposed proximal end;

a hub assembly located at said opposed proximal end;

a slot axially directed along the length of said hypodermic needle device from said distal end through said hub at said opposed proximal end said slot having a minimum width dimension; and an instrument having an instrument outer diameter, an instrument distal end and an instrument proximal end, inserted through said hub into said hypodermic needle device, said instrument comprising a hollow, cannulated stylet, and said slot minimum width dimension being less than said instrument outer diameter, and not less than a dimension through which said hollow cannulated stylet can pass therethrough.

3. The hypodermic needle device according to claim 2 wherein said hollow, cannulated stylet has a female luer fitting attached at said instrument proximal end a syringe being attachable to said female luer fitting of said hollow, cannulated stylet.

4. The hypodermic needle device according to claim 2 wherein said flexible catheter having a pre-affixed means for removably connecting said flexible catheter to a syringe attached at said instrument proximal end, whereby said flexible catheter is placed in fluid communication with a source of liquid anesthesia for administration to a patient.

5. An apparatus for administering regional anesthesia comprising:

a hypodermic needle having a barrel portion with inner and outer walls and a distal end and an opposed proximal end;

a slot axially directed along the length of said hypodermic needle from said distal end to said opposed proximal end, said slot having a minimum width dimension;

means for locating the epidural space of a patient using a hollow cannulated stylet inserted within said inner walls of said hypodermic needle;

means for identifying said locating of said epidural space and then removing said hollow cannulated stylet and replacing with a flexible catheter; and means for bringing said catheter into fluid communication with a source of liquid anesthesia for administration to a patient.

6. The apparatus according to claim 5 further comprising a hub assembly at said proximal end of said hypodermic needle; and a female luer fitting attached at a proximal end of said hollow, cannulated stylet wherein said means for identifying said locating of said epidural space is a syringe attached to said female luer fitting to locate the epidural space by observing a loss of resistance.

7. The apparatus according to claim 5 wherein said means for bringing said catheter into fluid communication with a source of liquid anesthesia for administration to a patient comprises:

a pre-affixed connector attached to said proximal end of said catheter whereby a syringe is removably connected to administer liquid anesthesia; and a removable cap attached to said connector such that said connector and said catheter are closed when not in use.

* * * * *